United States Patent
Modestas et al.

(10) Patent No.: US 8,404,219 B2
(45) Date of Patent: Mar. 26, 2013

(54) COMPOSITION FOR HAIR CARE

(75) Inventors: Algis C. Modestas, Palos Hills, IL (US); Ramesh C. Raval, Roselle, IL (US)

(73) Assignee: Namaste Laboratories, L.L.C., Blue Island, IL (US)

( * ) Notice: Subject to any disclaimer, the term of this patent is extended or adjusted under 35 U.S.C. 154(b) by 854 days.

(21) Appl. No.: 12/135,917

(22) Filed: Jun. 9, 2008

(65) Prior Publication Data

US 2009/0304619 A1     Dec. 10, 2009

(51) Int. Cl.
*A61K 8/72*     (2006.01)

(52) U.S. Cl. .................................................. 424/70.11

(58) Field of Classification Search ........................ None
See application file for complete search history.

(56) References Cited

U.S. PATENT DOCUMENTS

| | | | | |
|---|---|---|---|---|
| 5,976,514 | A * | 11/1999 | Guskey et al. | 424/65 |
| 6,326,011 | B1 * | 12/2001 | Miyazawa et al. | 424/401 |
| 7,101,538 | B1 * | 9/2006 | Tang | 424/70.1 |
| 2003/0152533 | A1 * | 8/2003 | Tang | 424/61 |

OTHER PUBLICATIONS

JP2006-069925, machine translation retrieved online on Jul. 18, 2011, p. 1-19.*

* cited by examiner

*Primary Examiner* — Blessing Fubara
*Assistant Examiner* — Jennifer Berrios
(74) *Attorney, Agent, or Firm* — McDermott Will & Emery LLP

(57) ABSTRACT

A hair care composition that includes a combination of chemical mixture that includes a perfluororoalkylethyl acrylate/hema copolymer, butyl acetate, and an aliphatic isoparaffin; and further includes an added amount of an aliphatic isoparraffin. Most preferred is 15 wt % to 35 wt % of the chemical mixture that includes the C6-C14 perfluororoalkylethyl acrylate/hema copolymer, and 65 wt % to 85 wt % of added C10-C14 aliphatic isoparaffin.

1 Claim, No Drawings

COMPOSITION FOR HAIR CARE

TECHNICAL FIELD

This invention is directed to a hair care composition for the protection of hair against the adverse effects of atmospheric moisture. For people with naturally curly hair, the product of the invention also appears to be able to alter, or at least maintain, the natural bonds of the hair. This enables the hair to maintain a straight condition, even in damp weather.

BACKGROUND OF THE INVENTION

Persons all over the world express themselves by, for example, changing the look, color, or texture of their hair. As but two examples, persons with straight hair will chemically treat it to make it curly, while persons with curly hair will chemically or thermally treat it to make it straight.

Many patents are directed to various kinds of hair care compositions. One such patent is U.S. Pat. No. 6,656,457. The '457 patent is directed to a hair care composition. A typical composition of the '457 patent requires water, a monohydric alcohol, and about 0.1 to about 10% of a "fixative styling polymer", which can include an acrylate copolymer. See col. 7, line 35-45, and col. 8, lines 15-16 and 32.

U.S. Pat. No. 6,187,302 is directed to a hair care composition for use in permanents. The claimed composition is directed to a first component comprising at least one thiol-bearing reducing agent in aqueous medium; and a second component comprising at least one thickening polymer in aqueous medium. Example 1 at column 6 of the '302 patent discloses that one of the two components (Part A) includes an acrylamide copolymer and isoparrafin. This Part A component is mixed with a Part B, and that Part B includes thioglycolic acid, diethaminetriamine pentaacetic acid, and other components.

U.S. Patent Application Publication No. 2007/0202067 is directed to an oil-in water emulsion. The claimed composition includes (a) an organopolysiloxane elastomer and (b) at least one thickener. Paragraph 20 of the '067 application discloses that at least one of its thickeners can include a mixture of polyacrylamide and a C13-C14 isoparaffin.

U.S. Patent Application Publication No. 2005/0136020 is directed to a hair care composition. The compositions and claims of the '020 application are directed to ethoxylated esters. See Paragraphs 0002 and 0036, and claims 1, 20, 37, and 45, each of which discloses the use of ethoxylated esters as a component.

Other patents directed to hair care products include U.S. Pat. No. 6,139,851. The '851 patent is directed to a hair cosmetic that comprises one or more silicone derivatives and one or more polyether modified silicones represented by the formula appearing at its column 18, lines 10-15.

U.S. Pat. No. 6,126,930 is directed to a hair care composition having between 60 and 99.9% alcohol. See clause (a) of each of independent claims 1, 16, and 17, at column 32 and 34, respectively.

U.S. Pat. No. 6,500,439 relates to a cosmetic composition directed to specific fluorine-containing copolymers. See claim 1, col. 33, lines 53-67; claim 8, column 36, lines 45-54; claim 10, col. 37, lines 30-42; claim 12, col. 38, line 61 through col. 39, line 7; and claim 39, col. 39, line 27 through col. 40, line 3.

U.S. Pat. No. 6,641,805 is directed to silicon- or silane-containing compositions. See independent claim 1, col. 23, lines 59-63.

U.S. Pat. No. 6,964,954 is directed to a composition including a DHEA derivative, and having the structure shown at independent claim 1, column 24, lines 1-51.

U.S. Pat. No. 6,071,504 is directed to a hair treatment composition having both a guanidium salt and a silicone.

Finally, the assignee of the present invention sold, beginning in 2003, a product that included 30 wt. % of Fibershield #4150, which is a C6-C14 perfluoroalkylethyl acrylate/hema copolymer; 35 wt. % hexamethyldisiloxane; and 35 wt % 200 proof ethyl alcohol. This product had an undesirable odor. In addition, as a result of the ethyl alcohol, this product had an undesirably high flash point. This had the potential for some danger in the event that the product was used with either blow dryers or heat wands.

SUMMARY OF THE INVENTION

The invention is a hair care composition. The composition is comprised of (a) a chemical mixture comprising a perfluororoalkylethyl acrylate/hema copolymer, butyl acetate, and an aliphatic isoparaffin; and (b) additional (or added) aliphatic isoparaffins.

Most preferably, the perfluororoalkylethyl acrylate/hema copolymerin in the chemical mixture is a C6-C14 perfluororoalkylethyl acrylate/hema copolymer. Most preferably, the aliphatic isoparaffin, whether it is inherent in the chemical mixture itself, or whether is added to the chemical mixture, is a C10-C14 aliphatic isoparaffin.

The most preferred range of the perfluoroalklylethyl acrylate/hema copolymer-containing chemical mixture is between 15 wt % and 35 wt %. Similarly, the most preferred range of the additional or added aliphatic isoparaffin is between 65 wt % and 85 wt %.

One preferred embodiment in accordance with the invention includes a C10-C13 aliphatic isoparaffin.

Still another preferred embodiment in accordance with the invention includes a C12 to C14 aliphatic isoparaffin.

In yet another preferred embodiment, the added aliphatic isoparaffin is present in an amount of between 70 wt % and 75 wt %.

In the most preferred embodiment of the invention, the added aliphatic isoparaffin is present in an amount of 70 wt %.

In addition, in the most preferred embodiment of the invention, the chemical mixture, containing the perfluoroalkylethyl acrylate/hema copolymer, is present in an amount of 30 wt %.

DETAILED DESCRIPTION

The description in this specification is intended to provide one or more examples of the principles of the invention. It is not intended to limit the scope of the invention. The scope of the invention is defined only by the correctly interpreted scope of the below claims.

The invention is a hair care composition. Preferably, the composition is comprised of a combination of (a) a chemical mixture that includes butyl acetate, at least one aliphatic isoparaffin, a perfluororoalkylethyl acrylate/hema copolymer, and (b) an additional amount of an aliphatic isoparaffin.

In connection with the present invention, the most preferred chemical mixture containing the perfluoroalkylethyl acrylate/hema copolymer is Fibershield #5480. Fibershield #5480 is a combination of a C6-C14 perfluoroalkylethyl acrylate/hema copolymer, butyl acetate, and one or more aliphatic isoparaffins. Fibershield #5480 is a product of Fiber-Shield Industries, Inc., 26 Old Dock Road, Yaphank, N.Y. 11980, tel. (631) 345 0240.

Preferably, the aliphatic isoparaffin is a C10-C14 aliphatic isoparaffin. This applies whether the isoparaffin is the component of the chemical mixture, or the added aliphatic isoparaffin. For the added aliphatic isoparaffin, the most preferred aliphatic isoparaffin is Soltrol #170, which is a C12-C14 aliphatic isoparaffin. Soltrol #170 is a product of Chevron Phillips Chemical Company LP, 10001 Six Pines Drive, The Woodlands, Tex. 77380.

Another preferred added aliphatic isoparaffin is Soltrol #130, which is a C10-C13 aliphatic isoparaffin. Soltrol #130 is also a product of the Chevron Phillips Chemical Company LP, 10001 Six Pines Drive, The Woodlands, Tex. 77380.

The most preferred range of the chemical mixture containing the perfluoroalklyethyl acrylate/hema copolymer is between 15 wt % and 35 wt %. Similarly, the most preferred range of the added aliphatic isoparaffin is between 65 wt % and 85 wt %.

In yet another preferred embodiment, the added aliphatic isoparaffin is present in an amount of between 70 wt % and 75 wt %.

In the most preferred embodiment of the invention, the added aliphatic isoparaffin is present in an amount of 70 wt %.

In addition, in the most preferred embodiment of the invention, the chemical mixture that contains the perfluoroalkylethyl acrylate/hema copolymer is present in an amount of 30 wt %.

The following Examples will provide details as to the manufacture of several compositions in accordance with the invention.

EXAMPLE 1

The individual chemical components of the present invention are mixed in accordance with common procedures. Particularly, a mixing kettle is used to blend the ingredients. Any of the kettles or other machines or equipment that will come into contact with the ingredients, including valves, pumps, hoses, and utensils, must be thoroughly cleaned, sanitized, rinsed, and dried before use.

In addition, the room or enclosure in which the mixing takes place must be relatively low in humidity.

These precautions are taken so that the finished product is a clear liquid is free of water. The individual chemical components used in connection with the present invention are sensitive to water. Thus, contact of those components with water can have an adverse effect.

To manufacture the product of the invention, 30.0 pounds of Fibershield 5480, which contains C6-C14 perfluoroalkylethyl acrylate/hema copolymer, butyl acetate, and aliphatic isoparaffin, is added to a mixing kettle.

Next, 70.0 pounds of a C12-C14 isoparaffin (Soltrol 170) is added to that kettle.

These, this chemical mixture and the added isoparaffin are blended for thirty (30) minutes to create a clear liquid, and the finished product.

The finished product is then pumped from, removed, or otherwise discharged from the mixing kettle.

The kettle and all equipment used in connection with the invention must be cleaned immediately. Failure to immediately and thoroughly clean the surfaces of both the kettle and the surfaces of the equipment that are used in the manufacture of the finished product will result in the formation upon those surfaces of a film that cannot be easily cleaned with either water or solvents.

EXAMPLE 2

Each of the procedures, equipment, and techniques used in Example 1 are used in this Example 2. The only difference is in the amounts of the chemical component ingredients.

Specifically, in this embodiment, 15.0 pounds of the chemical mixture containing C6-C14 perfluoroalkylethyl acrylate/hema copolymer is added to the kettle. Next, 85.0 pounds of an added C12-C14 isoparaffin (Soltrol 170) is added to the kettle.

EXAMPLE 3

Each of the procedures, equipment, and techniques used in Example 1 are used in this Example 3. The only difference is in the amounts of the ingredients.

Specifically, in this embodiment, 35.0 pounds of the chemical mixture containing C6-C14 perfluoroalkyl ethyl acrylate/hema copolymer is added to the kettle. Next, 65.0 pounds of an added or additional C12-C14 isoparaffin (Soltrol 170) is added to the kettle.

EXAMPLE 4

Each of the procedures, equipment, and techniques used in Example 1 are used in this Example 4. The only difference is in the amounts of the ingredients.

Specifically, in this embodiment, 25.0 pounds of a chemical mixture containing C6-C14 perfluoroalkyl ethyl acrylate/hema copolymer is added to the kettle. Next, 75.0 pounds of an additional C12-C14 isoparaffin (Soltrol 170) is added to the kettle.

EXAMPLE 5

Each of the procedures, equipment, and techniques used in Example 1 are used in this Example 5. The only difference is in the amounts of the ingredients.

Specifically, in this embodiment, 15.0 pounds of a chemical mixture containing C6-C14 perfluoroalkyl ethyl acrylate/hema copolymer is added to the kettle. Next, 85.0 pounds of an additional isoparaffin, here C12-C14 isoparaffin (Soltrol 170), is added to the kettle.

EXAMPLE 6

Each of the procedures, equipment, and techniques used in Example 1 are used in this Example 6. The only difference is in the type of ingredients.

Specifically, in this embodiment, 70.0 pounds of a C10-C13 isoparaffin (Soltrol 130) is substituted for the Soltrol 170.

It should be understood that this substitution of Soltrol 130 for Soltrol 170 can be made in any of the remaining Examples 2-5.

Products made in accordance with the invention are colorless and odorless. The addition of the isoparaffin results in a product that enables both better deposition, and a more uniform coating on the hair, as compared to the assignee's prior composition.

In addition, the product of the invention coats the hair fiber, and protects the hair against the deleterious effects of moisture. More particularly, the product of the invention protects permanent-treated hair against the deleterious effects of rain.

What is claimed is:

1. A hair-care composition consisting of:
    (a) 30.0 wt. % of a chemical mixture consisting of a C6-C14 perfluoroalkylethyl acrylate/hema copolymer, butyl acetate, and an aliphatic isoparaffin; and
    (b) 70.0 wt. % of added C12-C14 aliphatic isoparaffin.

* * * * *